United States Patent [19]

Couvreur et al.

[11] 4,329,332

[45] May 11, 1982

[54] BIODEGRADABLE SUBMICROSCOPIC PARTICLES CONTAINING A BIOLOGICALLY ACTIVE SUBSTANCE AND COMPOSITIONS CONTAINING THEM

[76] Inventors: Patrick Couvreur, 8, Avenue de la Forêt, 1970 Wezembeek-Oppem; Michel Roland, 38, rue Tomberg, 1150 Bruxelles, both of Belgium; Peter Speiser, 26Wassbergerstrasse, 8127 Forch, Switzerland

[21] Appl. No.: 57,767

[22] Filed: Jul. 16, 1979

[30] Foreign Application Priority Data

Jul. 19, 1978 [BE] Belgium ................... 189366

[51] Int. Cl.$^3$ .................... A61K 49/00; A61J 3/00; A61K 9/26; B01J 13/02
[52] U.S. Cl. ........................... 424/9; 252/316; 424/1; 424/7; 424/22; 424/33; 424/88; 424/89; 424/92; 424/93; 424/94
[58] Field of Search ............. 252/316; 424/33, 9, 424/22, 1; 526/297

[56] References Cited

U.S. PATENT DOCUMENTS

| | | | |
|---|---|---|---|
| 2,776,232 | 1/1957 | Shearer, Jr. et al. | 526/297 X |
| 2,912,454 | 11/1959 | McKeever | 260/465.4 |
| 3,185,625 | 5/1965 | Brown | 424/35 X |
| 3,415,758 | 12/1968 | Powell et al. | 252/316 |
| 3,544,500 | 12/1970 | Osmond et al. | 252/316 X |
| 3,660,304 | 5/1972 | Matsukawa | 252/316 |
| 4,107,288 | 8/1978 | Oppenheim et al. | 252/316 X |

FOREIGN PATENT DOCUMENTS

| | | | |
|---|---|---|---|
| 1572106 | 5/1969 | France | 424/35 |
| 49-34299 | 9/1974 | Japan | 252/316 |
| 1516348 | 7/1978 | United Kingdom | 252/316 |

OTHER PUBLICATIONS

Coover, Jr. et al.: "Chemistry and Performance of Cyanoacrylate Adhesives", Soc. Plastics Eng. J., 15–413 (1959).
Donnelly et al.: "Ionic and Zwitterionic Polymerization of N-Alkyl-2-Cyanoacrylates", Polymer Letters Edition, vol. 15, pp. 399–405 (1977).
Couvreur et al.: "Nanokapseln: Ein Neuer Lysosomotropischer Träger", Acta Pharmaceutica Technologica, Supplement 7/1978.
Couvreur et al.: "Nanocapsules: A New Type of Lysosomotropic Carrier", Febs Letters, 84(2): 323–326, (1977).
Couvreur et al.: "Adsorption of Antineoplastic Drugs to Polyalkylcyanoacrylate Nanoparticles . . . ", J. of Pharmaceutical Sciences, vol. 68, No. 12, Dec. 1979.
Couvreur et al.: "Tissue Distribution of Antitumor Drugs Associated with Polyalkylcyanoacrylate Nanoparticles", J. of Pharmaceutical Sciences, vol. 69, No. 2, Feb. 1980 (199–202).
Kante et al.: "Tissue Distribution of [$^3$H] Actinomycin D Adsorbed on PolybutylcyanoacrylateNanoparticles," Internat'l. J. of Pharmaceutics, 7 (1980), 45–53.
Brasseur et al.: "Actinomycin D Adsorbed on Polymethylcyanoacrylate Nanoparticles: . . . ", Europ. J. Cancer, vol. 16, pp. 1441–1445, (1980).
Clayton: "Colloid Aspects of Food Chemistry and Technology", J. & A. Churchill, London, 1932, p. 116.
Winnacker et al.: "Chemie Organique", Paris, 1969, p. 583.
Birrenbach et al.: "Polymerized Micelles . . . ", J. of Pharmaceutical Sciences, vol. 65, No. 12, Dec. 1976, pp. 1763–1766.
Chem. Abstracts, vol. 83, No. 3, Aug. 1975, p. 305, 48195h and 48196j, (Tomoegawa).
Chem. Abstracts, vol. 88, No. 18, May 1978, p. 322, 126303m, (Couvreur et al.).
Chem. Abstracts, vol. 88, No. 24, Jun. 1978, p. 426, 177057s, (Marty et al.).
Chem. Abstracts, vol. 89, No. 8, Aug. 1978, p. 334, 65167s, (Kreuter).

*Primary Examiner*—Richard D. Lovering
*Attorney, Agent, or Firm*—Beveridge, DeGrandi & Kline

[57] ABSTRACT

Biodegradable particles, with a diameter smaller than 500 nanometers, formed by the micellar polymerization of an alkyl-cyano-acrylate where the term "alkyl" means a lower alkyl radical having 1 to 4 carbon atoms and containing a biologically active substance.

12 Claims, 3 Drawing Figures

BIODEGRADABLE SUBMICROSCOPIC PARTICLES CONTAINING A BIOLOGICALLY ACTIVE SUBSTANCE AND COMPOSITIONS CONTAINING THEM

This invention relates to submicroscopic particles, formed from a polymerized alkyl cyano-acrylate and containing a biologically active substance, their preparation and application.

Particles with a diameter smaller than 500 nanometers and formed from a polymerized material are known as well as their preparation and application especially as supports for biologically active substances. Thus, Belgian Pat. Nos. 808,034 and 839,748 describe submicroscopic particles formed from polymerizable materials such as derivatives of acrylic or methacrylic acids for example methyl methacrylate, butyl methacrylate, methacrylamide or a mixture of these compounds. Submicroscopic particles, formed by the micellar polymerization of these various monomers, have two properties, namely (1) they can envelop completely or partially the biologically active substance and (2) they can form colloidal aqueous solutions which allow the parenteral dispensing of these particles thus charged with biologically active substances.

However, the aforesaid polymers of acrylic or methacrylic acids for the preparation of submicroscopic particles containing a biologically active substance are substantially stable so that they remain without change for a long time in the tissues or cavity in which they are dispensed. This constitutes a drawback, especially in the case of parenteral dispensing in humans.

The present invention remedies this drawback by using as starting material polymers of alkyl-cyano-acrylates. These polymers which are already used in surgery as tissue and hemostatic adhesives, are definitely biodegradable.

In the electron microscope (FIGS. 1 and 2, see below) the submicroscopic particles in accordance with the invention are in the shape of a ball having a very dense polymeric, more or less spherical, network with a diameter smaller than 500 nanometers and preferably smaller than 200 nanometers. The particles are formed by the polymerization of alkyl-cyano-acrylate where the term "alkyl" indicates a lower alkyl radical containing from 1 to 4 carbon atoms and especially the methyl radical.

The particles according to the invention contain inside their filamentous network a biologically active substance which could be, for example, a medicinal substance for human or veterinary use or a product for diagnosis. As medicinal substances there may be specifically mentioned chemicals with pharmacological properties and, for example, antimitotic or antineoplastic drugs such as methotrexate, actinomycin D, adriamycin, daunorubicin, bleomycin and vincristine; antibiotics such as penicillins, cephalosporins and nalidixic acid; antibiotics of the aminoglycoside type and those of the virginiamycine family and hormonal substances, especially steroid hormones. These medicinal products may be, in particular, chemical compounds with a high molecular weight such as insulin, and heparin and the "medicinal substances" comprise also biological products such as antigens, allergens, enzymes, proteins, viruses or elements found in viruses, bacteria or cells. The submicroscopic particles according to the invention may also contain a product for diagnosis such as fluorescein and radioactive human seralbumin.

In human or veterinary medicine, the submicroscopic particles according to the invention can be dispensed with an appropriate excipient, orally, subcutaneously, intradermally, intramuscularly or intravenously and because of their diffusion in the tissues they are particularly suitable for general treatment.

The present invention will be further illustrated by way of the accompanying drawings in which:

FIG. 3 is a graph showing the kinetics at play when actinomycin D is released from nanospherules of polyalkylcyanoacrylate in a serum medium (percentages on the Y axis and time in hours on the X axis) in which:

(1) curve A relates to the polymethylcyanoacrylate (2) curve B relates to a 2:1 mixture of polymethyl- and polyethylcyanoacrylate (3) curve C relates to a 1:1 mixture of polymethyl- and polyethylcyanoacrylate (4) curve D relates to a 1:2 mixture of polymethyl- and polyethylcyanoacrylate and (5) curve E relates to polyethylcyanoacrylate.

Figure 3:
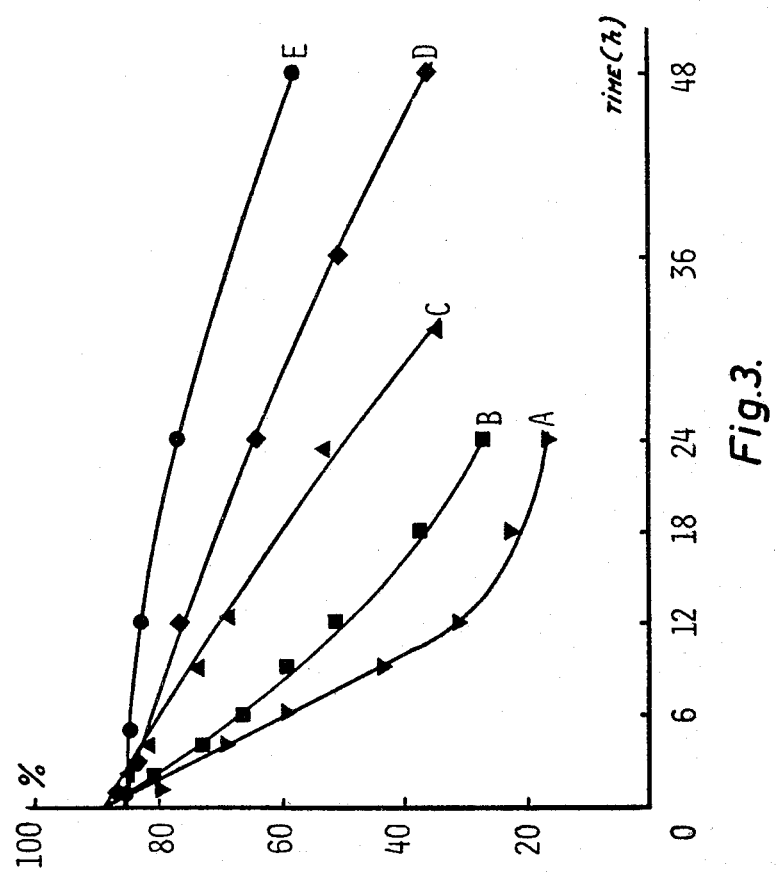

Consequently, the dispensing of submicroscopic particles according to the invention is followed by a progressive release of the biologically active substance in relation to the biodegradability of the polymerized material. Since the biodegradability of alkylpolycyanoacrylates, depends on the nature of the alkyl chain, it is possible to choose a product, the polymerized form of which has a biodegradability corresponding to the program established for releasing the biologically active material. Thus, the degradability kinetics of these nanoparticles in a serum medium as well as the release of the adsorbed drug can be perfectly controlled and programmed according to the therapeutic effect desired. This objective can be reached by using appropriate mixtures of nanospheres (FIG. 3).

Another advantage of alkyl cyanoacrylates over other acrylic derivatives previously used for preparing submicroscopic particles containing a biologically active substance rests in the process which can be used to polymerize the monomers. Indeed, contrary to other acrylic derivatives the polymerization of which requires an energy contribution liable to harm the stability of the adsorbed active principle, alkyl cyanoacrylates may be easily polymerized without such a contribution.

In the process according to the invention for the preparation of submicroscopic particles, the monomer is added to the aqueous solution of a surface active agent, preferably a non-ionic surface active agent such as for example, the monolaurate of polyhydroxyethylated sorbitan, subjected to a vigorous agitation so as to form a micellar solution the pH of which is adjusted to a value lower than 7 and preferably between 2 and 3, with a pharmacologically acceptable acid such as, for example, hydrochloric, hydrobromic, hydroiodic, sulfuric, phosphoric, acetic, succinic or lactic acid insofar as the acid is compatible with the medium components, that is to say its action should not run counter to the actions of these components and especially not the action of the surface-active agent. The alkyl-cyano-acrylate is polymerized at the room temperature or even at a temperature lower than the usual temperature and the biologically active substance is introduced into the medium either before the introduction of the monomer or after polymerization. The pH of the medium adjusts both polymerization rate and the adsorption degree of the biologically active material when the latter is in an ionized form.

It is to be noted that the polymerization process is slowed down when the pH is reduced and that the adsorption of the biologically active material reaches a maximum when it is in a highly lipophilic form, that is to say non-ionized or else when the medium pH corresponds to the pKa value of the biologically active substance. In practice, it is possible to reconcile these two requirements by carrying out first the polymerization at a pH making it possible to control the reaction, i.e. preferably at a pH value between 2 and 3 and by carrying out the adsorption after polymerization, adjusting then, if necessary, the medium pH so that its value will correspond to the pKa of the biologically active substance.

The invention is further illustrated by the following Examples.

EXAMPLE 1

In 45.5 milliliters (ml) of distilled water, 180 milligrams (mg) of monolaurate of polyhydroxyethylated sorbitan, 4.5 ml of hydrochloric acid (0.1 N) and 1 mg of tritiated actinomycin D are dissolved and 0.83 ml of methyl-cyano-acrylate is added slowly with vigorous agitation. The agitation is maintained for 30 minutes after the complete monomer addition. The polymerization which takes place spontaneously makes the suspension opalescent at first and gives it then a milky appearance. The reaction medium is buffered to pH7 by means of a few drops of normal caustic soda and by 5 ml of phosphate buffer (30 ml of monopotassium phosphate (0.2 M) and 30 ml sodium hydroxide (0.2 M) adjusted to 200 ml) and centrifuged at 50,000 g.

By radioactive dosing (liquid scintillation) in the supernatant liquid and in the centrifugation residue, it is possible to ascertain that the quantity of actinomycin D attached to the particles corresponds to 90% of the quantity used. The examination of the particles by means of an electron microscope after cryofracture discloses that they are of a substantially spherical shape with a diameter less than 200 nanometers.

EXAMPLE 2

In 45.5 mls of distilled water are dissolved 180 mg of the monolaurate of polyhydroxyethylated sorbitan, 4.5 ml of hydrochloric acid (0.1 N) and 1 mg of triturated actinomycin D and then 0.83 ml of ethyl cyanoacrylate is added with vigorous stirring. The agitation is continued for 1 hour after the complete addition of the monomer. The reaction medium is filtered through fritted glass for which the pores have a diameter between 9 and 15 microns and the filtrate is adjusted to pH7 by a few drops of 1 N caustic soda and phosphate buffer (50 ml of monopotassium phosphate (0.2 M) and 30 ml of sodium hydroxide (0.2 M) adjusted to 200 ml) and centrifuged at 50,000 g.

By radioactive dosing (liquid scintillation) in the supernatant and in the centrifugation residue it is possible to ascertain that the quantity of actinomycin D attached to the particles corresponds to 85% of the quantity used. In a scanning electron microscope it can be seen that particles have a structure and a dimension identical to those of particles obtained in Example 1.

EXAMPLE 3

In 30 ml of hydrochloric acid (0.1 N), 300 mg of the monolaurate of polyhydroxyethylated sorbitan and 1 mg of actinomycin D are dissolved and the technique of Example 1 is subsequently followed with 0.5 ml of methyl-cyano-acrylate. Under these conditions, particles which are comparable to those obtained in Example 1 are obtained. The diameter of the particles is generally between 300 and 500 nanometers.

EXAMPLE 4

In 30 ml of distilled water, 3 ml of hydrochloric acid (0.1 N) and respectively 50, 100, 200, 300 and 700 mg of the monolaurate of polyhydroxyethylated sorbitan are dissolved. Slowly and with a vigorous agitation, 0.5 ml of methyl cyanoacrylate is added and then the procedure of Example 1 is followed. At the end of each operation, particles morphologically and granulometrically identical to the particles obtained in Example 1 are obtained.

EXAMPLE 5

Figure 1:
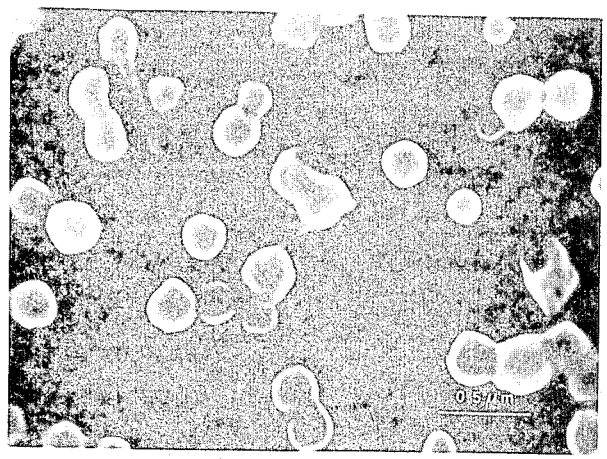
FIG. 1 is a microphotograph (scanning electron microscope) showing the morphological aspect of nanoparticles of polyalkylcyanoacrylates.
Figure 2:
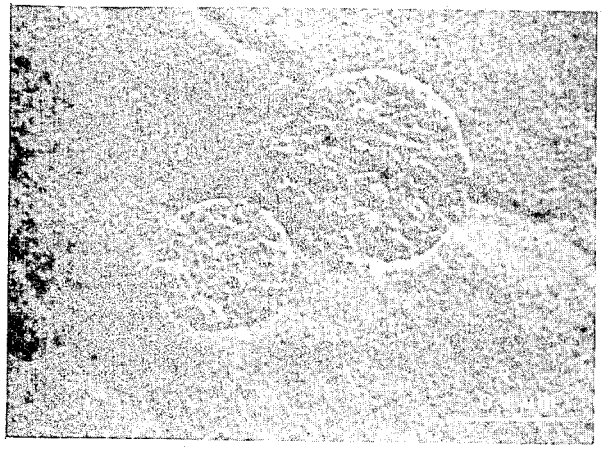
FIG. 2 is a microphotograph (electron microscope) showing the internal structure of nanoparticles of polyalkylcyanoacrylate after cryofracture.

The procedure described in Example 1 is followed but without introducing actinomycin D. Under these conditions particles without active substance are obtained which, when examined under an electron microscope after cryofracture, have a more or less spherical shape the diameter of which is smaller than 200 nanometers and an internal structure made up of a very dense polymeric network with a large specific surface. These nanospheres do not have external coverings and they cannot, therefore, be classed as nanocapsules (FIG. 2).

EXAMPLE 6

In 45.5 ml of distilled water, 80 mg of the monolaurate of polyhydroxyethylated sorbitan and 4.5 ml of hydrochloric acid (0.1 N) are dissolved. Then 0.83 ml of methyl-cyano-acrylate is slowly added with vigorous agitation. The agitation is kept for 30 minutes after the complete addition of monomer. The medium is buffered to pH7 by means of a few drops of normal caustic soda and by 5 ml of phosphate buffer (50 ml of monopotassium phosphate (0.2 M) and 30 ml of sodium hydroxide (0.2 N) adjusted to 200 ml and 1 mg of tritiated actinomycin D is added with agitation. The medium is kept agitated for 30 minutes and it is then centrifuged at 50,000 g.

By dosing (liquid scintillation) actinomycin D in the supernatant and in the centrifugation residue, it is noted that the quantity of actinomycin D attached to the particles corresponds to 66% of the quantity used.

EXAMPLE 7

In 50 ml of distilled water, 250 mg of the monolaurate of polyhydroxyethylated sorbitan, 5 ml of hydrochloric acid (0.1 N) and 10 mg of fluorescein are dissolved then 0.6 ml of ethyl-cyano-acrylate is added slowly with vigorous agitation. The agitation is continued for 30 minutes after the complete monomer addition. The suspension is then diluted to 200 ml by adding distilled water. The medium is then centrifuged at 50,000 g. By means of a fluorometric dosing of fluorescein in the supernatant and in the centrifugation residue it is noted that the quantity of fluorescein attached to the particles is approximately 65-70% of the quantity used.

EXAMPLE 8

In 45 ml of distilled water, 200 mg of the monolaurate of polyhydroxyethylated sorbitan, 5 ml of hydrochloric acid (0.1 N) and 5 mg of methotrexate are dissolved. Then 0.83 ml of methyl-cyano-acrylate is added slowly with vigorous agitation, the agitation continuing for 30 minutes after the complete addition of monomer. Twenty (20) ml of the suspension are buffered to pH7 by means of a few drops of normal caustic soda and of a phosphate buffer (50 ml of monopotassium phosphate (0.2 M) and 30 ml of sodium hydroxide (0.2 N) adjusted to 200 ml) so as to bring the suspension to 25 ml. The medium is then centrifuged at 50,000 g.

With fluorometric dosing of methotrexate in the supernatant and in the centrifugation residue, it is to be noted that the quantity of methotrexate attached to the particles corresponds approximately to 25% ($\pm 5\%$) of the quantity used.

EXAMPLE 9

In 50 ml of distilled water, 250 mg of the monolaurate of polyhydroxyethylated sorbitan, 5 ml of hydrochloric acid (0.1 N) and 10 mg of daunorubicin are dissolved. Then 0.6 ml of methyl-cyano-acrylate is slowly added with vigorous agitation, (the agitation continuing for 30 minutes after the complete addition of the monomer). The medium is then adjusted to 100 ml by the addition of distilled water and the suspension is buffered to pH9 by adding a few drops of bicarbonate of soda (1 M) and it is adjusted to 200 ml by a borate buffer at pH9 (50 ml of a boric acid/potassium chloride mixture (0.2 M) and 21 ml of sodium hydroxide (0.2 N) adjusted to 200 ml) and centrifuged at 50,000 g.

A fluorometric dosing of daunorubicin in the supernatant and in the centrifugation residue, makes it possible to determine that the quantity of daunorubicin attached to the particles correspond to about 85% of the quantity used.

EXAMPLE 10

In 50 ml of sterile and apyrogenic distilled water, 200 mg of the monolaurate of polyhydroxyethylated sorbitan, 5 ml of hydrochloric acid (0.1 N) and 5 mg of actinomycin D are dissolved. Then 0.83 ml of methyl-cyano-acrylate is added with vigorous agitation. The medium is adjusted to pH7 by means of a few drops of normal caustic soda and phosphate buffer (50 ml of monopotassium phosphate (0.2 M) and 30 ml of sodium hydroxide (0.2 N) adjusted to 200 ml). The medium is then sterilized, filtered and distributed among glass phials at the rate of 0.5 mg of actinomycin D per phial. The phials are hermetically closed and stored away from light. They contain unitary doses of actinomycin D suitable for local parenteral dispensing or for intravenous perfusion after reconstitution in an isotonic diluent of an appropriate type for any one of these dispensing methods.

EXAMPLE 11

In 45.5 ml of distilled water, 180 mg of the monolaurate of polyhydroxyethylated sorbitan and 4.5 ml of hydrochloric acid (0.1 N) are dissolved. About 800 mg of amylose are added to this solution. The suspension is then heated to about 80° C. and is kept at that temperature until the complete dissolution of amylose occurs. The solution is then cooled and filtered. Fifty ml of propylene glycol are then mixed with this solution and 0.5 ml of butyl-cyano-acrylate is added with agitation. The agitation is continued for 4 hours after completing the addition of the monomer. The medium is then buffered to pH7 by means of a few drops of normal caustic soda and of 10 ml of phosphate buffer (50 ml of monopotassium phosphate (0.2 M) and 30 ml of sodium hydroxide (0.2 N) adjusted to 200 ml).

EXAMPLE 12

In 45.5 ml of distilled water, 180 mg of the monolaurate of polyhydroxyethylated sorbitan and 4.5 ml of hydrochloric acid (0.1 N) are dissolved. An alkyl-cyano-acrylate (methyl or ethyl) is added slowly with vigorous agitation (0.83 ml). The agitation is continued for 1 hour after completing the addition of the monomer. After that, 250 UI of insulin is dissolved in the suspension of nanoparticles thus formed. After a one hour contact, the reaction medium is buffered to pH7 by means of a few drops of normal caustic soda and of 5 ml of phosphate buffer (50 ml of monopotassium phosphate (0.2 M) and 30 ml of sodium hydroxide (0.2 N) adjusted to 200 ml) and centrifuged at 50,000 g.

By means of a radioimmunological dosage of insulin in the supernatant and in the centrifugation residue, it is possible to determine that the quantity of insulin attached to the nanoparticles corresponds to 80% of the quantity used in the case of polymethylcyanoacrylate nanoparticles and to 75% of the same quantity in the case of polyethylcyanoacrylate nanoparticles.

After dispensing subcutaneously the latter to male WHISTAR R rats made diabetic previously by an intraperitoneal injection of alloxan, a hypoglycemic effect was obtained for 24 hours.

EXAMPLE 13

In 45.5 ml of distilled water, 180 mg of the monolaurate of polyhydroxyethylated sorbitan, 4.5 ml of hydrochloric acid (0.1 N) and 17.5 mg of tritium-tagged vinblastine are dissolved. With vigorous agitation, 0.83 ml of ethyl-cyano-acrylate is added. The agitation is continued for one hour after the complete addition of the monomer. The reaction medium is buffered to pH7 by means of a few drops of normal caustic soda and of 5 ml of phosphate buffer (50 ml of monopotassium phosphate (0.2 M) and 30 ml of sodium hydroxide (0.2 N) adjusted to 200 ml) and centrifuged at 50,000 g.

A radioactive dosage (liquid scintillation) in the supernatant liquid and in the centrifugation residue makes it possible to determine that the quantity of vinblastine attached to the particles correspond to about 70% of the quantity used before polymerizing.

When vinblastine is associated with polyethylcyanoacrylate nanoparticles, the corporeal distribution of this medicine is notably modified after it has been dispensed intravenously to male WHISTAR R rats. A tissular concentration much higher than that of the pure product is observed in the liver, spleen, lungs and muscles.

EXAMPLE 14

In 45.5 ml of distilled water, 180 mg of the monolaurate of polyhydroxyethylated sorbitan, 4.5 ml of hydrochloric acid (0.1 N) and 40 mg of Levamisole chlorohydrate are dissolved. Slowly and with vigorous agitation 0.750 ml methyl-cyano-acrylate is added. The agitation is continued for half an hour after the complete addition of the monomer. The reaction medium is then buffered to pH7 by means of a few drops of normal caustic soda and of 5 ml of phosphate buffer. After 24 hours the suspension is centrifuged to 50,000 g.

With a spectrophotometric dosage (at 212 nm) of Levamisole in the supernatant liquid and in the centrifugation residue it is possible to determine that the quantity of active principle attached to the nanoparticles corresponds to 25% of the quantity involved.

EXAMPLE 15

In 45.5 ml of distilled water, 180 mg of the monolaurate of polyhydroxyethylated sorbitan, 4.5 ml of hydrochloric acid (0.1 N) and 50 mg of potassium V penicillin are dissolved. Slowly and with vigorous agitation, 0.800 ml of methyl-cyano-acrylate is added. The agitation is continued for half an hour after the complete addition of the monomer. The reaction medium is then buffered to pH7 by means of a few drops of normal caustic soda and with 5 ml of phosphate buffer. The suspension is then centrifuged at 50,000 g.

By means of a spectrophotometric dosage (at 325 nm after a degradation of penicillin with imidazole and a reaction with $HgCl_2$) of penicillin V in the supernatant liquid, it is possible to determine that the quantity of active principle attached to nanoparticles correspond to about 50% of the quantity involved.

The embodiments of the invention in which an exclusive property or privilege is claimed are defined as follows:

1. Biodegradable particles having a diameter less than 500 nanometers for oral or parenteral administration in a human or animal host, said particles comprising a substantially spherical, dense, filamentous, polymeric network, wherein the polymeric network has dispersed therethrough a biologically active substance, and wherein said polymer is biodegradable in said host and is formed by the micellar polymerization of an alkyl cyano-acrylate said alkyl group containing 1 to 4 carbon atoms, and when said polymer particles are biodegraded in said host, the biologically active substance is progressively released into said host at a rate substantially corresponding to the rate of biodegradation of said polymer.

2. Biodegradable particles according to claim 1, which have a diameter of less than 200 nanometers.

3. Biodegradable particles according to claim 1 or 2 in which the biologically active substance is a product with antimitotic, antineoplastic, antibiotic or hormonal properties, a virus, a virus component, a bacterium component, a cell component, an antigen, an allergen or an enzyme.

4. A pharmaceutical composition containing biodegradable particles as defined according to claim 3 and an excipient for orally, subcutaneously, intradermally, intramuscularly or intraveneously administering said composition.

5. Biodegradable particles according to claim 1 or 2 formed by the polymerization of methyl-cyano-acrylate.

6. A pharmaceutical composition containing biodegradable particles as defined according to claim 5 and an excipient for orally, subcutaneously, intradermally, intramusuclarly or intraveneously administering said composition.

7. Biodegradable particles according to claim 5 in which the biologically active substance is a product with antimitotic, antineoplastic, antibiotic or hormonal properties, a virus, a virus component, a bacterium component, a cell component, an antigen, an allergen or an enzyme.

8. A pharmaceutical composition containing biodegradable particles as defined according to claims 1, 2 or 5 and an excipient for orally, subcutaneously, intradermally, intramuscularly or intraveneously administering said composition.

9. Biodegradable particles having a diameter less than 500 nanometers for parenteral administration in a human or animal host, said particles comprising a substantially spherical, dense, filamentous, polymeric network wherein the polymeric network has dispersed therethrough a biologically active substance, and wherein said polymer is biodegradable in said host and is formed by the micellar polymerization of an alkyl cyano-acrylate in an aqueous solution of a non-ionic surface active agent and at a pH less than 7, said alkyl containing 1 to 4 carbon atoms, and when said polymer particles are biodegraded in said host, the biologically active substance is progressively released into said host at a rate substantially corresponding to the rate of biodegradation of said polymer.

10. Biodegradable particles according to claim 9 in the form of a mixture of nanoparticles formed from different alkyl cyano-acrylates to thereby provide nanoparticles in said mixture having different degradability kinetics in the host.

11. Biodegradable particles having a diameter less than 500 nanometers for use as a diagnostic agent, said particles comprising a substantially spherical, dense, filamentous, polymeric network wherein the polymeric network has dispersed therethrough a biologically active substance, and wherein said polymer is biodegradable and is formed by the micellar polymerization of an alkyl cyano-acrylate in an aqueous solution of a surface active agent and at a pH less than 7, said alkyl containing 1 to 4 carbon atoms, and wherein said polymer particles are biodegraded in use as a diagnostic agent whereby the biologically active substance is progressively released at a rate substantially corresponding to the rate of biodegradation of said polymer.

12. Biodegradable particles according to claim 11 in the form of a mixture of nanoparticles formed from different alkyl cyano-acrylates to thereby provide nanoparticles in said mixture having different degradability kinetics.

* * * * *